United States Patent [19]

Hutchins

[11] 4,119,660

[45] Oct. 10, 1978

[54] METHOD FOR MAKING DIPEROXYACIDS

[75] Inventor: James Peyton Hutchins, Springfield Township, Hamilton County, Ohio

[73] Assignee: The Procter & Gamble Company, Cincinnati, Ohio

[21] Appl. No.: 818,897

[22] Filed: Jul. 25, 1977

Related U.S. Application Data

[63] Continuation-in-part of Ser. No. 718,281, Aug. 27, 1976, abandoned.

[51] Int. Cl.² .......................................... C07C 179/10
[52] U.S. Cl. .............................................. 260/502 R
[58] Field of Search .................................. 260/502 R

[56] References Cited

U.S. PATENT DOCUMENTS

| | | | |
|---|---|---|---|
| 2,813,896 | 11/1957 | Krimm | 260/502 R |
| 3,079,411 | 2/1963 | Silbert et al. | 260/502 R |
| 3,819,688 | 6/1974 | Silbert et al. | 260/502 R |

FOREIGN PATENT DOCUMENTS 635,620  1/1962  Canada ................................ 260/502 R

OTHER PUBLICATIONS

Parker et al.; J. Amer. Chem. Soc., vol. 79, p. 1929 (1957).
Reeve et al., J. Amer. Chem. Soc., vol. 79, p. 1932 (1957).

*Primary Examiner*—James O. Thomas, Jr.
*Assistant Examiner*—Werren B. Lone
*Attorney, Agent, or Firm*—Douglas C. Mohl; George M. Kaplan; Richard C. Witte

[57] ABSTRACT

A process for making aliphatic diperoxyacids comprising adding a dibasic acid having from 12 to 20 carbon atoms to a solution of from about 6% to about 14% hydrogen peroxide, about 69% to about 82% sulfuric acid and about 6% to about 21% water.

5 Claims, No Drawings

METHOD FOR MAKING DIPEROXYACIDS

CROSS-REFERENCE TO RELATED APPLICATION

This application is a continuation-in-part of application Ser. No. 718,281, entitled "Method for Making Diperoxyacids," filed Aug. 27, 1976 and now abandoned.

BACKGROUND OF THE INVENTION

The present invention is related to an improved method for making aliphatic diperoxyacids having from about 12 to about 20 carbon atoms.

Peroxygen bleaching agents in general and peroxyacid compounds in particular have long been recognized as effective bleaching agents for use when the adverse color and fabric damage effects of harsh halogen active bleaching agents cannot be tolerated. See, for example, Canadian Pat. No. 632,620, Jan. 30, 1962, to McCune. This attractive nature of peroxy-acid compounds makes it desirable to be able to make them in the most economical manner.

The prior art teaches the making of peroxyacid compounds in several ways. Parker et al in *Journal American Chemical Society*, 79, 1929 (1957), disclose making diperoxyacids by dissolving a dibasic acid in sulfuric acid and adding hydrogen peroxide dropwise. U.S. Pat. No. 3,079,411, Feb. 26, 1963, to Silbert et al., discloses forming long chain aliphatic peroxyacids by combining an aliphatic acid with an alkanesulfonic acid and then treating the combination with an excess of hydrogen peroxide. U.S. Pat. No. 2,813,896, Nov. 19, 1957, to Krimm, discloses forming peroxyacids by combining sulfuric acid and hydrogen peroxide and subsequently treating the combination with carboxylic acid. The reaction is conducted so that there is at least one mole of sulfuric acid present at the end of the reaction for every six moles of water.

While the prior art teaches several methods for making peroxyacids, it does not indicate what problems are involved with making long chain peroxyacids. It has been found that using the prior art methods, such acids are formed slowly or in very small, difficult to filter crystals.

It is an object of the present invention to provide a method for making diperoxyacids which overcomes the above problems. Specifically, the present invention provides a method whereby diperoxyacids can be made much quicker than prior art methods or in larger, easier to filter crystals.

These and other objects of the present invention will become apparent from the following description.

All percentages and ratios used herein are by weight unless otherwise specified.

SUMMARY OF THE INVENTION

The present invention relates to a process for making aliphatic diperoxyacids comprising adding a dibasic acid having from about 12 to about 20 carbon atoms to a solution containing from about 6% to about 14% hydrogen peroxide, about 69% to about 82% sulfuric acid and about 6% to about 21% water.

DETAILED DESCRIPTION OF THE INVENTION

The process of the present invention involves the following steps:

A. Forming a solution containing from about 6% to about 14% hydrogen peroxide, about 69% to about 82% sulfuric acid and about 6% to about 21% water.

B. Adding to the solution of A an aliphatic dibasic carboxylic acid having the formula

wherein R is an alkylene group having from about 10 to about 18 carbon atoms to form a mixture. In a preferred process the dibasic caroxylic acid is added slowly over a time period of from about 30 to about 120 minutes.

C. Maintaining the mixture of B at a temperature of from about 10° C. to about 50° C. until the diperoxyacid crystals are formed. Preferably the mixture is maintained at the desired temperature for a period of from about 1 to about 4 hours after all of the dibasic acid has been added.

D. Recovering the diperoxyacid crystals of step C by means of filtration.

E. Washing the crystals with water and drying said crystals.

The diperoxyacid formed using the above-described method is formed quickly and under certain conditions (e.g., low temperature, slow addition of the dibasic acid, and/or small amount of hydrogen peroxide) the crystals formed are very easily filtered. The method also provides for a safer, more easily controlled reaction since the strongly exothermic mixing of hydrogen peroxide, water and sulfuric acid can be done before the unstable diperoxy acid is formed. For example, the mixing of the three liquid components can be done in a vessel separate from the one in which the diperoxyacid is formed.

The ingredients used in the process of the present invention are all readily available in commerce. Hydrogen peroxide can be of any concentration, but is preferably from about 35% to about 70%, while sulfuric acid is preferably used in a concentration of from about 92% to about 98%. The percentages of these materials in the reaction mixture described above are based on pure materials.

The acids suitable for use herein are those aliphatic dibasic carboxylic acids having from about 12 to about 20 carbon atoms. The unsubstituted acids have the following general formula:

wherein R is an alkylene group containing from about 10 to about 18 carbon atoms. Preferred R groups are of the formula $-(CH_2)_n-$ wherein $n$ is a number of from about 10 to about 14. Especially preferred is dodecanedioic acid ($n = 10$).

While it is true as indicated above that the levels of water, sulfuric acid and hydrogen peroxide can be within the ranges given, there exist preferred ranges for these three materials which vary with the chain length of the aliphatic dibasic acid employed. These ranges are shown below for some of the preferred acids.

| Acid | % Water | % Sulfuric Acid | % Hydrogen Peroxide |
|---|---|---|---|
| $HO-\overset{O}{\underset{\|}{C}}-(CH_2)_{10}-\overset{O}{\underset{\|}{C}}-OH$ | 16-21 | 69-75 | 8-14 |
| $HO-\overset{O}{\underset{\|}{C}}-(CH_2)_{11}-\overset{O}{\underset{\|}{C}}-OH$ | 9-14 | 76-80 | 8-14 |
| $HO-\overset{O}{\underset{\|}{C}}-(CH_2)_{12}-\overset{O}{\underset{\|}{C}}-OH$ | 8-13 | 78-82 | 8-14 |

In a preferred method the water and hydrogen peroxide are mixed together, cooled to about 5° C. to about 15° C. and the sulfuric acid is added dropwise.

The amount of dibasic acid used in the present process varies with the actual amount of hydrogen peroxide used. The relationship is as follows:

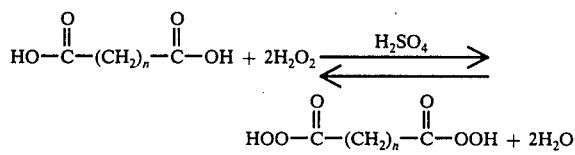

It is preferred, however, that hydrogen peroxide be used in an amount which is 25% or more in excess of the stoichiometric amount required.

The peroxyacids made using the process of the present invention can be dried using conventional drying techniques with usual safeguards for handling peroxyacids being observed.

COMPOSITIONS CONTAINING THE PEROXYACID COMPOUNDS

The peroxyacid compounds made using the process of the present invention can be used in a wide variety of compositions. A preferred use is as a fabric bleaching agent. To insure that compositions containing the peroxyacid compounds are safe and effective, certain additives are desirably present.

It is well documented in the peroxyacid literature that peroxyacids are susceptible to a number of different stability problems, as well as being likely to cause some problems. Looking at the latter first, peroxyacids decompose exothermally and when the material is in dry granular form the heated generated must be controlled to make the product safe. The best exotherm control agents are those which are capable of liberating moisture at a temperature slightly below the decomposition temperature of the peroxyacid employed. U.S. Pat. No. 3,770,816, Nov. 6, 1973, to Nielsen, incorporated herein by reference, discloses a wide variety of hydrated materials which can serve as suitable exotherm control agents. Included among such materials are magnesium sulfate ·7H$_2$O, magnesium formate dihydrate, calcium sulfate (CaSO$_4$·2H$_2$O), calcium lactate hydrate, calcium sodium sulfate (CaSO$_4$·2Na$_2$SO$_4$·2H$_2$O), and hydrated forms of such things as sodium aluminum sulfate, potassium aluminum sulfate, ammonium aluminum sulfate and aluminum sulfate. Preferred hydrates are the alkali metal aluminum sulfates, particularly preferred is potassium aluminum sulfate. Other preferred exotherm control agents are those materials which lose water as the result of chemical decomposition such as boric acid, malic acid and maleic acid. The exotherm control agent is preferably used in an amount of from about 100% to about 200% based on the weight of the peroxyacid compound.

The other problems faced when peroxyacid compounds are used fall into the area of maintaining good bleach effectiveness. It has been recognized that metal ions are capable of serving as catalyzing agents in the degradation of the peroxyacid compounds. To overcome this problem chelating agents can be used in an amount ranging from 0.005% to about 1.00% based on the weight of the composition to tie up heavy metal ions. U.S. Pat. No. 3,442,937, May 6, 1969, to Sennewald et al., discloses a chelating system comprising quinoline or a salt thereof, an alkali metal polyphosphate and, optionally, a synergistic amount of urea. U.S. Pat. No. 2,838,459, June 10, 1958, to Sprout, Jr., discloses a variety of polyphosphates as stabilizing agents for peroxide baths. These materials are useful herein as stabilizing aids. U.S. Pat. No. 3,192,255, June 29, 1965, to Cann, discloses the use of quinaldic acid to stabilize percarboxylic acids. This material, as well as picolinic acid and dipicolinic acid, would also be useful in the compositions of the present invention. A preferred chelating system for the present invention is a mixture of 8-hydroxyquinoline and an acid polyphosphate, preferably acid sodium pyrophosphate. The latter can be a mixture of phosphoric acid and sodium pyrophosphate wherein the ratio of the former to the latter is from about 0.5:1 to about 2:1 and the ratio of the mixture to 8-hydroxyquinoline is from about 1:1 to about 5:1.

In addition to the above-mentioned chelating systems to tie up heavy metals in the peroxyacid compositions, coating materials may also be used to extend the shelf life of dry granular compositions. Such coating materials may be, in general, acids, esters, ethers and hydrocarbons and include such things as wide varieties of fatty acids, derivatives of fatty alcohols, such as esters and ethers, derivatives of polyethyleneglycols such as esters and ethers and hydrocarbon oils and waxes. These materials aid in preventing moisture from reaching the peracid compound. Secondly, the coating material may be used to segregate the peracid compound from other agents which may be present in the composition and adversely affect the peracid's stability. When used in this manner the coating may be used on both the peracid compound and the other agent or either individually. The amount of the coating material used is generally from about 2.5% to about 15% based on the weight of the peroxyacid compound.

Additional agents which may be used to aid in giving good bleaching performance include such things as pH adjustment agents, bleach activators and minors such as coloring agents, dyes and perfumes. Typical pH adjustment agents are used to alter or maintain aqueous solutions of the instant compositions within the 5 to 10 pH range in which peroxyacid bleaching agents are generally most useful. Depending upon the nature of other optional composition ingredients, pH adjustment agents can be either of the acid or base type. Examples of acidic pH adjustment agents designed to compensate for the presence of other highly alkaline materials include normally solid organic and inorganic acids, acid mixtures and acid salts. Examples of such acidic pH adjustment agents include citric acid, glycolic acid, tartaric acid, gluconic acid, glutamic acid, sulfamic acid, sodium bisulfate, potassium bisulfate, ammonium bisulfate and mixtures of citric acid and lauric acid. Citric acid is preferred by virtue of its low toxicity and hardness sequestering capability.

Optional alkaline pH adjustment agents include the conventional alkaline buffering agents. Examples of such buffering agents include such salts as carbonates, bicarbonates, silicates, pyrophosphates and mixtures thereof. Sodium bicarbonate and tetrasodium pyrophosphate are highly preferred.

Optional peroxyacid bleach activators as suggested by the prior art include such materials as aldehydes and ketones. Use of these materials as bleaching activators is described more fully in U.S. Pat. No. 3,822,114, July 2, 1974, to Montgomery, incorporated herein by reference.

A preferred dry, granular bleaching product employing the peroxyacid bleach of the present invention involves combining the active peroxy compound with potassium aluminum sulfate or boric acid and the acid pyrophosphate/8-hydroxyquinoline subsequently coating this mixture with mineral oil and agglomerating the coated particles with a polyethylene glycol derivative. An alkaline pH adjustment agent is then added to the agglomerated stabilized active as a dry mix.

Optional ingredients, if utilized in combination with the active peroxyacid of the instant invention to form a complete bleaching product, comprise from about 20% to about 99% weight of the total composition. Conversely, the peroxyacid compound made using the process of the present invention comprises from about 1% to about 80% of the composition.

The bleaching compositions of the instant invention, particularly the dry granular version, can also be added to and made a part of conventional fabric laundering detergent compositions. Accordingly, optional materials for the instant bleaching compositions can include such standard detergent adjuvants as surfactants and builders. Optional surfactants are selected from the group consisting of organic anionic, nonionic, ampholytic, and zwitterionic surfactants and mixtures thereof. Optional builder materials include any of the conventional organic and inorganic builder salts including carbonates, silicates, acetates, polycarboxylates and phosphates. If the instant stabilized bleaching compositions are employed as part of a conventional fabric laundering detergent composition, the instant bleaching agent generally comprises from about 1% to about 40% by weight of such conventional detergent compositions. Conversely, the instant bleaching compositions can optionally contain from about 60% to about 99% by weight of conventional surfactant and builder materials. Further examples of suitable surfactants and builders are given below.

Water-soluble salts of the higher fatty acids, i.e., "soaps," are useful as the anionic surfactant herein. This class of surfactants includes ordinary alkali metal soaps such as the sodium, potassium, ammonium and alkanolammonium salts of higher fatty acids containing from about 8 to about 24 carbon atoms and preferably from about 10 to about 20 carbon atoms. Soaps can be made by direct saponification of fats and oils or by the neutralization of free fatty acids. Particularly useful are the sodium and potassium salts of the mixtures of fatty acids derived from coconut oil and tallow, i.e., sodium or potassium tallow and coconut soaps.

Another class of anionic surfactants includes water-soluble salts, particularly the alkali metal, ammonium and alkanolammonium salts, of organic sulfuric reaction products having in their molecular structure an alkyl group containing from about 8 to about 22 carbon atoms and a sulfonic acid or sulfuric acid ester group. (Included in the term "alkyl" is the alkyl portion of acyl groups.) Examples of this group of synthetic surfactants which can be used in the present detergent compositions are the sodium and potassium alkyl sulfates, especially those obtained by sulfating the higher alcohols ($C_8$–$C_{18}$ carbon atoms) produced by reducing the glycerides of tallow or coconut oil; and sodium and potassium alkyl benzene sulfonates, in which the alkyl group contains from about 9 to about 15 carbon atoms in straight chain or branched chain configuration, e.g., those of the type described in U.S. Pat. Nos. 2,220,099, and 2,477,383, incorporated herein by reference.

Other anionic surfactant compounds useful herein include the sodium alkyl glyceryl ether sulfonates, especially those ethers or higher alcohols derived from tallow and coconut oil; sodium coconut oil fatty acid monoglyceride sulfonates and sulfates; and sodium or potassium salts of alkyl phenol ethylene oxide ether sulfate containing about 1 to about 10 units of ethylene oxide per molecule and wherein the alkyl groups contain about 8 to about 12 carbon atoms.

Other useful anionic surfactants herein include the water-soluble salts of esters of α-sulfonated fatty acids containing from about 6 to 20 carbon atoms in the ester group; water-soluble salts of 2-acyloxy-alkane-1-sulfonic acids containing from about 2 to 9 carbon atoms in the acyl group and from about 9 to about 23 carbon atoms in the alkane moiety; alkyl ether sulfates containing from about 10 to 20 carbon atoms in the alkyl group and from about 1 to 30 moles of ethylene oxide; water-soluble salts of olefin sulfonates containing from about 12 to 24 carbon atoms; and β-alkyloxy alkane sulfonates containing from about 1 to 3 carbon atoms in the alkyl group and from about 8 to 20 carbon atoms in the alkane moiety.

Preferred water-soluble anionic organic surfactants herein include linear alkyl benzene sulfonates containing from about 11 to 14 carbon atoms in the alkyl group; the tallow range alkyl sulfates; the coconut range alkyl glyceryl sulfonates; and alkyl ether sulfates wherein the alkyl moiety contains from about 14 to 18 carbon atoms and wherein the average degree of ethoxylation varies between 1 and 6.

Specific preferred anionic surfactants for use herein include: sodium linear $C_{10}$–$C_{12}$ alkyl benzene sulfonate; triethanolamine $C_{10}$–$C_{12}$ alkyl benzene sulfonate; sodium tallow alkyl sulfate; sodium coconut alkyl glyceryl ether sulfonate; and the sodium salt of a sulfated condensation product of tallow alcohol with from about 3 to about 10 moles of ethylene oxide.

It is to be recognized that any of the foregoing anionic surfactants can be used separately herein or as mixtures.

Nonionic surfactants include the water-soluble ethoxylates of $C_{10}$–$C_{20}$ aliphatic alcohols and $C_6$–$C_{12}$ alkyl phenols. Many nonionic surfactants are especially suitable for use as suds controlling agents in combination with anionic surfactants of the type disclosed herein.

Semi-polar surfactants useful herein include water-soluble amine oxides containing one alkyl moiety of from about 10 to 28 carbon atoms and 2 moieties selected from the group consisting of alkyl groups and hydroxyalkyl groups containing from 1 to about 3 carbon atoms; water-soluble phosphine oxides containing one alkyl moiety of about 10 to 28 carbon atoms and 2 moieties selected from the group consisting of alkyl groups and hydroxyalkyl groups containing from about 1 to 3 carbon atoms; and water-soluble sulfoxides containing one alkyl moiety of from about 10 to 28 carbon atoms and a moiety selected from the group consisting of alkyl and hydroxyalkyl moieties of from 1 to 3 carbon atoms.

Ampholytic surfactants include derivaties of aliphatic or aliphatic derivatives of heterocyclic secondary and tertiary amines in which the aliphatic moiety can be straight chain or branched and wherein one of the aliphatic substituents contains from about 8 to 18 carbon atoms and at least one aliphatic substituent contains an anionic water-solubilizing group.

Zwitterionic surfactants include derivatives of aliphatic quaternary ammonium, phosphonium and sulfonium compounds in which the aliphatic moieties can be straight or branched chain, and wherein one of the aliphatic substituents contains from about 8 to 18 carbon atoms and one contains an anionic water-solubilizing group.

The instant granular compositions can also comprise those detergency builders commonly taught for use in laundry compositions. Useful builders herein include any of the conventional inorganic and organic water-soluble builder salts, as well as various water-insoluble and so-called "seeded" builders.

Inorganic detergency builders useful herein include, for example, water-soluble salts of phosphates, pyrophosphates, orthophosphates, polyphosphates, phosphonates, carbonates, bicarbonates, borates and silicates. Specific examples of inorganic phosphate builders include sodium and potassium tripolyphosphates, phosphates, and hexametaphosphates. The polyphosphonates specifically include, for example, the sodium and potassium salts of ethylene diphosphonic acid, the sodium and potassium salts of ethane 1-hydroxy-1,1-diphosphonic acid, and the sodium and potassium salts of ethane-1,1,2-triphosphonic acid. Examples of these and other phosphorus builder compounds are disclosed in U.S. Pat. Nos. 3,159,581; 3,213,030; 3,422,021; 3,422,137; 3,400,176 and 3,400,148, incorporated herein by reference. Sodium tripolyphosphate is an especially preferred, water-soluble inorganic builder herein.

Non-phosphorus containing sequestrants can also be selected for use herein as detergency builders. Specific examples of non-phosphorus, inorganic builder ingredients include water-soluble inorganic carbonate, bicarbonate, borate and silicate salts. The alkali metal, e.g., sodium and potassium, carbonates, bicarbonates, borates (Borax) and silicates are particularly useful herein.

Water-soluble, organic builders are also useful herein. For example, the alkali metal, ammonium and substituted ammonium polyacetates, carboxylates, polycarboxylates, succinates, and polyhydroxysulfonates are useful builders in the present compositions and processes. Specific examples of the polyacetate and polycarboxylate builder salts include sodium, potassium, lithium, ammonium and substituted ammonium salts of ethylene diamine tetraacetic acid, nitrilotriacetic acid, oxydisuccinic acid, mellitic acid, benzene polycarboxylic acids, and citric acid.

Highly preferred non-phosphorous builder materials (both organic and inorganic) herein include sodium carbonate, sodium bicarbonate, sodium silicate, sodium citrate, sodium oxydisuccinate, sodium mellitate, sodium nitrilotriacetate, and sodium ethylenediaminetetraacetate, and mixtures thereof.

Another type of detergency builder material useful in the present compositions and processes comprises a water-soluble material capable of forming a water-insoluble reaction product with water hardness cations in combination with a crystallization seed which is capable of providing growth sites for said reaction product.

Specific examples of materials capable of forming the water-insoluble reaction product include the water-soluble salts of carbonates, bicarbonates, sequicarbonates, silicates, aluminates and oxalates. The alkali metal, especially sodium, salts of the foregoing materials are preferred for convenience and economy.

Another type of builder useful herein includes various substantially water-insoluble materials which are capable of reducing the hardness content of laundering liquors, e.g., by ion-exchange processes. Examples of such builder materials include the phosphorylated cloths disclosed in U.S. Pat. No. 3,424,545, Bauman, issued Jan. 28, 1969, incorporated herein by reference.

The complex aluminosilicates, i.e., zeolite-type materials, are useful presoaking/washing adjuvants herein in that these materials soften water, i.e., remove $Ca^{++}$ hardness. Both the naturally occurring and synthetic "zeolites", especially zeolite A and hydrated zeolite A materials, are useful for this builder/softener purpose. A description of zeolite materials and a method of preparation appears in Milton, U.S. Pat. No. 2,882,243, issued Apr. 14, 1959, incorporated herein by reference.

COMPOSITION PREPARATION

The bleaching compositions of the instant invention are prepared in any conventional manner such as by admixing ingredients, by agglomeration, by compaction or by granulation in the case of the dry granule form. In one method for preparing such compositions, a peroxyacid-water mixture containing from about 50% by weight to about 80% by weight of water is combined in proper proportions with any optional components to be utilized within the bleaching granules themselves. Such a combination of ingredients is then thoroughly mixed and subsequently run through an extruder. Extrudate in the form of noodles is then fed into a spheronizer (also known by the trade name, Marumerizer) to form approximately spherical particles from the peroxyacid-containing noodles. The bleaching granules can then be dried to the appropriate water content. Upon leaving the spheronizer, such particles are screened to provide uniform particle size.

Bleaching granules prepared in this manner can then be admixed with other granules of optional bleaching or detergent composition materials. Actual particle size of either the bleach-containing granules or optional granules of additional material is not critical. If, however, compositions are to be realized having commercially acceptable flow properties, certain granule size limitations are highly preferred. In general, all granules of the instant compositions preferably range in size from about 100 microns to 3000 microns, more preferably from about 100 microns to 1300 microns.

Additionally, flowability is enhanced if particles of the present invention are of approximately the same size. Therefore, preferably the ratio of the average particle sizes of the bleach-containing granules and optional granules of other materials varies between 0.5:1 and 2.0:1.

Bleaching compositions of the present invention are utilized by dissolving them in water in an amount sufficient to provide from about 1.0 ppm to 100 ppm available oxygen in solution. Generally, this amounts to about 0.01% to 0.2% by weight of composition in solution. Fabrics to be bleached are then contacted with such aqueous bleaching solutions.

The bleaching compositions of the instant invention are illustrated by the following examples:

EXAMPLE I

An example of the process of the present invention is as follows:

An open beaker is charged with 13.3 grams of hydrogen peroxide (100%) and 28.1 grams of water. This solution is cooled to below 10° C. and 120 grams of sulfuric acid (100%) are added dropwise. This premix is warmed to 35° C. and 30 grams of powdered dodecanedioic acid are added with stirring. The reaction mixture is maintained at a temperature of 35° C. Samples are taken at various times and treated as follows: the samples are quenched immediately in an excess of ice water; the product crystals formed are washed with water and dried; and the product is analyzed by conventional iodometric techniques for available oxygen. It is found that conversion from the dibasic acid to the diperoxyacid is quickly achieved using the above conditions.

EXAMPLE II

The process as described in Example I is repeated using 8.35 grams of hydrogen peroxide, 14.1 grams of water, 80 grams of sulfuric acid and 20 grams of a powdered form of the acid

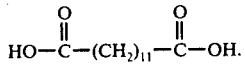

The diperoxyacid is formed quickly.

EXAMPLE III

The process of Example I is repeated using 7.9 grams of hydrogen peroxide, 13 grams of water, 80 grams of sulfuric acid and 20 grams of the powdered acid

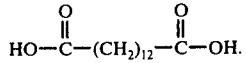

The diperoxyacid is formed quickly.

What is claimed is:

1. A process for making aliphatic diperoxyacids comprising the following steps:
  A. Forming a solution containing from about 6% to about 14% hydrogen peroxide, about 69% to about 82% sulfuric acid and about 6% to about 21% water,
  B. Adding to the solution of A an aliphatic dibasic carboxylic acid having the formula

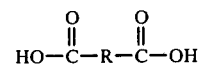

wherein R is an alkylene group containing from about 10 to 18 carbon atoms to form a mixture,
  C. Maintaining the mixture of B at a temperature of from about 10° C. to about 50° C. until the peroxyacid crystals are formed,
  D. Recovering the diperoxyacid crystals of step C by means of filtration; and
  E. Washing the diperoxyacid crystals with water and drying said crystals.

2. A process according to claim 1 wherein the mixture of step B is maintained at a temperature of from about 10° C. to about 50° C. for a period of about 1 hour to about 4 hours.

3. A process according to claim 1 wherein the amount of hydrogen peroxide is from about 8% to about 14%, the amount of sulfuric acid is from about 69% to about 75%, the amount of water is from about 16% to about 21% and the dibasic acid has the formula

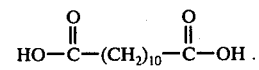

4. A process according to claim 1 wherein the amount of hydrogen peroxide is from about 8% to about 14%, the amount of sulfuric acid is from about 76% to about 80%, the amount of water is from about 9% to about 14% and the dibasic acid has the formula

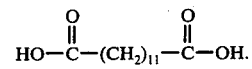

5. A process according to claim 1 wherein the amount of hydrogen peroxide is from about 8% to about 14%, the amount of sulfuric acid is from about 78% to about 82%, the amount of water is from about 8% to about 13% and the dibasic acid has the formula

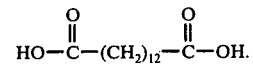

* * * * *